United States Patent [19]

Kawai et al.

[11] 4,255,592

[45] Mar. 10, 1981

[54] PROCESS FOR PRODUCING AROMATIC PRIMARY HYDROPEROXIDE

[75] Inventors: Yoshio Kawai, Niigata; Koichi Kida, Toyosaka; Hideo Ikarashi, Niigata; Tsukasa Toki, Niigata; Yoshiharu Suzuki, Niigata, all of Japan

[73] Assignee: Mitsubishi Gas Chemical Company, Inc., Tokyo, Japan

[21] Appl. No.: 79,330

[22] Filed: Sep. 27, 1979

[30] Foreign Application Priority Data

Oct. 3, 1978 [JP] Japan .................. 53-121643

[51] Int. Cl.$^3$ ............................................. C07C 179/035
[52] U.S. Cl. ...................................... 568/573; 568/569
[58] Field of Search ........................ 568/573, 572, 569

[56] References Cited

U.S. PATENT DOCUMENTS

| 2,661,375 | 12/1953 | Conner | 568/573 |
| 2,683,751 | 7/1954 | Filar | 568/573 |
| 2,773,906 | 12/1956 | Emerson | 568/573 |

FOREIGN PATENT DOCUMENTS 48-34846  5/1973  Japan .

345137  8/1973  U.S.S.R. .................. 568/573

OTHER PUBLICATIONS

Tanaka, "Chemistry Letters" pp. 1347–1348 (1974) Pub. Chemical Soc. of Japan.
Lorand et al., "J. A. C. S." vol. 77, pp. 4035–4037 (1955).
Hock et al., "Chem. Abstract" vol. 37, p. 5382 (1943).

*Primary Examiner*—Werren B. Lone
*Attorney, Agent, or Firm*—Armstrong, Nikaido, Marmelstein & Kubovcik

[57] ABSTRACT

An aromatic primary hydroperoxide is produced by oxidizing a methyl-substituted aromatic compound in a liquid phase with a molecular oxygen-containing gas at a temperature of 80°–150° C. under a pressure of the atmospheric to 100 kg/cm$^2$ gage in the presence of 8–300 parts by weight of an aliphatic tertiary hydroperoxide per 100 parts by weight of the methyl-substituted aromatic compound. The oxidation reaction is promoted, an aromatic primary hydroperoxide content of the reaction products is increased, whereas by-products are reduced, and a selectivity to the aromatic primary hydroperoxide is considerably increased.

11 Claims, No Drawings

PROCESS FOR PRODUCING AROMATIC PRIMARY HYDROPEROXIDE

This invention relates to a process for producing an aromatic primary hydroperoxide by oxidation of a nuclear-substituted methyl group.

An aromatic primary hydroperoxide having a $CH_2OOH$ group on its aromatic nucleus (which will be hereinafter referred to as "1-HPO") is useful, because, for example, benzyl hydroperoxide, methylbenzyl hydroperoxide and dimethylbenzyl hydroperoxide can produce phenol, cresol and xylenol correspondingly by decomposition.

A process for producing 1-HPO by autooxidation of nuclear-substituted methyl group of the methyl-substituted aromatic compound is known, but a hydrogen atom on α-position in the nuclear-substituted methyl group is hardly taken away, as compared with that in the nuclear-substituted ethyl group and nuclear-substituted isopropyl group. Therefore, it is much more difficult to obtain the primary hydroperoxide from the methyl-substituted aromatic compound than to obtain a secondary hydroperoxide or a tertiary hydroperoxide from an ethyl-substituted aromatic compound or an isopropyl-substituted aromatic compound correspondingly, and consequently it is necessary to elevate a reaction temperature or prolong a reaction time.

Furthermore, the resulting 1-HPO has such a high reactivity that it is readily decomposed and sensitive to metal, acid and alkali. That is, aldehydes, alcohols, carboxylic acids, unknown by-products of high boiling points are much produced at the same time beside 1-HPO, and consequently a selectivity of the starting material to 1-HPO is much reduced.

As regards the production of 1-HPO by the autooxidation of methyl-substituted aromatic compound, various processes comprising making various substances as an initiator, etc. in the reaction system have been so far proposed. For example, U.S. Pat. NO. 2,683,751 discloses a process comprising oxidizing an aromatic compound having a methyl group with a molecular oxygen-containing gas in a liquid phase, thereby obtaining 1-HPO, and then decomposing 1-HPO to a corresponding phenol, where peroxides such as di-t-butyl peroxide (which will be hereinafter referred to as "D-t-BPO"), α,α-dimethyl-p-methylbenzyl hydroperoxide, cumene hydroperoxide, etc., are used as an initiator in the oxidation step of obtaining 1-HPO. However, no disclosure is made of the yield in the oxidation reaction, but according to trace tests conducted by the present inventors, it has been found that, for example, when 100 parts by weight of p-xylene and 10 -parts by weight of D-t-BPO are subjected to reaction at 135° C. under the atmospheric pressure for 2 hours according to Example 1 of the U.S. Patent a conversion of p-xylene is only 7.3%, and a selectivity to p-methylbenzyl hydroperoxide (which will be hereinafter referred to as PX-HPO) is only 48%.

Journal of Americal Chemical Society 77 4,035 discloses a process for producing PX-HPO from p-xylene, comprising initially adding 100 g of D-t-BPO as an initiator to 1,000 g of p-xylene, and 50 g of D-t-BPO at every one hour to make a total of 200 g of D-t-BPO, while conducting reaction at 120°-130° C. for 2.25 hours, where a maximum yield of PX-HPO is only 4.2% by mole on the basis of starting material p-xylene.

The results of these prior art processes show that D-t-BPO, etc. are effective for initiating the reaction, but not effective for enhancing the selectivity to 1-HPO, even though the amount of D-t-BPO, etc. to be added is increased.

On the other hand, Japanese Laid-open Pat. Application No. 34846/73 and Chemical Letters 1,347 (1974) disclose processes for producing PX-HPO from p-xylene, comprising using benzoyl peroxide, azobisbutyronitrile, D-t-BPO, t-butyl perbenzoate, or the like as a reaction initiator, and further making a nitrile compound present in the reaction system, where a selectivity to 1-HPO is higher than in the above-mentioned process; for example, when an equal amount of benzonitrile is added to p-xylene, and reaction is carried out at 150° C. for 5 hours, a conversion of p-xylene amounts to 7.04%, and a selectivity to PX-HPO amounts to 70.2%. However, when a conversion of p-xylene is increased to more than 10%, a selectivity to PX-HOP is decreased to less than 60%, and as a result the yield is low.

As described above, the yield of 1-HPO and the selectivity to 1-HPO are low in the prior art processes, and these prior art processes are directed mostly to p-xylene. In the case of other aromatic compounds containing the methyl group, for example, toluene, m-xylene, and mesitylene, the yield of 1-HPO is much lower.

As a result of extensive studies to overcome these disadvantages of the prior art processes, the present inventors have found that 1-HPO can be obtained with a high selectivity by adding a large amount of an aliphatic tertiary hydroperoxide (which will be hereinafter referred to as "t-HPO") to the reaction system, thereby suppressing an occurrence of side reaction.

The present invention provides a process for producing 1-HPO by oxidizing a methyl-substituted aromatic compound in a liquid phase with a molecular oxygen-containing gas, which comprises carrying out the oxidation in the presence of 8–300 parts by weight, preferably 8–100 parts by weight, of t-HPO per 100 parts by weight of the methyl-substituted aromatic compound.

When the amount of t-HPO is below the lower limit of said range, the effect is low, whereas when it exceeds the upper limit of said range, an amount of decomposed t-HPO is increased, sometimes bringing about a fear of explosion. Thus, the amount of t-HPO outside said range is not preferable.

t-HPO represented by the following general formula is effective:

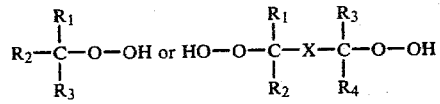

wherein $R_1$, $R_2$, $R_3$ and $R_4$ each represent alkyl groups having 1 to 4 carbon atoms, cycloalkyl groups, or cycloalkyl groups having an alkyl group of 1 to 4 carbon atoms as a substituent and X represents alkylene groups having 1 to 4 carbon atoms. More specifically, as t-HPO, t-butyl hydroperoxide (which will be hereinafter referred to as "t-BHPO"), p-methane hydroperoxide, and 2,5-dimethylhexane-2,5-dihydroperoxide can be mentioned. Two or more of these t-HPOs can be used at the same time, or they can be added to the reaction system in the form of a solution.

The autooxidation reaction of the present invention is carried out by blowing a molecular oxygen-containing gas into a starting material methyl-substituted aromatic compound containing t-HPO in a liquid phase under the atmospheric or superatmospheric pressure.

As suitable starting material methyl-substituted aromatic compound, toluene, o-xylene, m-xylene, p-xylene, mesitylene and pseudocumene can be mentioned, and correspondingly, benzyl hydroperoxide, o-methylbenzyl hydroperoxide, m-methylbenzyl hydroperoxide, p-methylbenzyl hydroperoxide, 3,5-dimethylbenzyl hydroperoxide, and dimethylbenzyl hydroperoxide mixture (mixture of 2,4-, 3,4- and 2,5-isomers) can be obtained therefrom.

The reaction can be carried out batchwise, semi-batchwise or continuously.

Reaction temperature is 80°-150° C., preferably 100°-140° C. The reaction rate is very low, if the reaction temperature is below the lower limit of said range, whereas when it exceeds the upper limit of said range, a consecutive reaction from 1-HPO takes place. Thus, the reaction temperature outside said range is not preferable.

Reaction pressure depends upon the kind of the starting material and t-HPO, but is in a range of atmospheric pressure to 100 kg/cm$^2$ gage, preferably 2-30 kg/cm$^2$ gage.

As the molecular oxygen-containing gas, pure oxygen gas or a mixture of oxygen with an inert gas can be used, but air is preferable. In order to attain a sufficient contact of the liquid with the gas in a reactor, it is preferable to stir the reaction solution or supply the gas as fine bubbles into the reaction solution.

The lower a conversion of the starting material methyl-substituted aromatic compound, the higher a selectivity, but an appropriate conversion is about 5-25% in an industrial scale operation, and it is preferable to adjust reaction time or residence time to attain such conversion.

It is also preferable to use an initiator together with t-HPO, for example, a radical reaction initiator generally having a lower heat decomposition temperature than that of t-HPO, for example, di-t-butyl peroxide, azobisisobutyronitrile and benzoyl peroxide, but even if it is not used together with t-HPO, a portion of t-HPO is decomposed to play a role of the initiator at the same time, and thus the reaction can be initiated.

However, the addition of the initiator can shorten an induction period in the case of batch reaction, and consequently it is not necessary to elevate the reaction-initiating temperature. In the continuous reaction, a stationary radical concentration can be kept, and thus it is not necessary to use the initiator. In the batch reaction, an appropriate amount of the radical reaction initiator is 0.1-5 parts by weight per 100 parts by weight of the starting material methyl-substituted aromatic compound.

As materials of construction for the reactor for carrying out the present reaction, it is preferable to use such stable one against 1-HPO as glass, polyfluoroethylene resin, or titanium, aluminum, zirconium, and their alloys.

According to the present invention, the oxidation reaction is promoted, a 1-HPO content of the reaction products is increased, whereas by-products are reduced, and a selectivity to 1-HPO is considerably increased. Furthermore, consumption of t-HPO added is negligible.

Said effects cannot be obtained even by using said peroxide such as D-t-BPO, azobisisobutyronitrile, benzoyl peroxide, etc. as the ordinary initiator at the same concentration as t-HPO, and rather an adverse effect will be obtained in the case of these ordinary initiators.

The present invention will be described in detail below, referring to Examples and Comparative Examples.

EXAMPLE 1

200 G of p-xylene and 100 g of a t-BHPO solution consisting of 81.3% by weight of t-BHPO, 5% by weight of DBPO, and 13.7% by weight of water were charged into a titanium autoclave with a stirrer and subjected to reaction at a reaction temperature of 120° C. under a reaction pressure of 10 kg/cm$^2$ gage with stirring at 1,000 rpm for 2 hours, while blowing air at a flow rate of 20 l/hr into the reaction solution, whereby 305 g of reaction product solution was obtained.

p-Xylene consumed amounted to 24.9 g, PX-HPO formed 24.7 g, p-tolualdehyde formed 1.1 g, and p-toluic acid 1.37 g.

| | |
|---|---|
| p-xylene conversion: | 12.5% |
| Selectivity to PX-HPO: | 76.1% |
| Selectivity to p-tolualdehyde: | 3.8% |
| Selectivity to p-toluic acid: | 4.3% |

The remaining t-BHPO in the reaction product solution amounted to 80.3 g, whereas t-BHPO consumed amounted to as small as 1.0 g.

EXAMPLES 2-8

Oxidation was carried out batchwise in the same manner as in Example 1 while changing conditions to various degrees. The results are shown in Table 1.

In Examples 2-6 and 8, t-BHPO was used in the same solution form as in Example 1, where the amount added was in the weight as the solution. p-menthane hydroperoxide used in Example 7 had a purity of 98%.

TABLE 1

| Ex. No. | 2 | 3 | 4 | 5 | 6 | 7 | 8 |
|---|---|---|---|---|---|---|---|
| Kind of starting material | toluene | m-xylene | m-xylene | m-xylene | mesitylene | mesitylene | mesitylene |
| t-HPO | t-BHPO | t-BHPO | t-BHPO | t-BHPO | t-BHPO | p-menthane-hydroperoxide | t-BHPO |
| Starting material charged g | 200 | 240 | 200 | 150 | 100 | 240 | 270 |
| t-HPO charged g | 100 | 60 | 100 | 150 | 100 | 60 | 30 |
| Reaction pressure kg/cm$^2$ gage | 10 | 10 | 20 | 5.0 | 10 | 30 | 10 |
| Reaction temp. °C. | 120 | 130 | 120 | 100 | 115 | 120 | 130 |
| Air flow rate l/hr | 10 | 20 | 10 | 20 | 25 | 50 | 50 |
| Reaction time hr | 4.0 | 2.0 | 4.0 | 2.0 | 3.0 | 4.0 | 2.0 |
| Reaction product solution g | 306.0 | 304.1 | 305.9 | 304.2 | 203.8 | 303.9 | 304.2 |
| Starting material consumed g | 17.1 | 19.7 | 24.4 | 20.2 | 15.6 | 31.9 | 30.5 |
| t-HPO consumed g | 3.0 | 1.9 | 2.7 | 0.6 | 1.1 | 0.9 | 1.2 |

TABLE 1-continued

| Ex. No. | 2 | 3 | 4 | 5 | 6 | 7 | 8 |
|---|---|---|---|---|---|---|---|
| l-HPO formed g | 13.0 | 20.4 | 24.5 | 22.1 | 15.2 | 29.5 | 25.5 |
| Conversion % | 8.6 | 8.2 | 12.2 | 13.5 | 15.6 | 13.3 | 11.3 |
| Selectivity to l-HPO % | 56.4 | 79.5 | 77.1 | 84.0 | 78.0 | 73.0 | 66.0 |
| Reaction material | titanium | titanium | titanium | pressure glass | aluminum | titanium | aluminum |

EXAMPLE 9

Four reactor vessels, each having a net capacity of 300 ml, were connected to one another in series, and reaction solution in the respective reactor vessels was kept in a completely mixed state and the respective amount was kept to 150 g, so that the amount over 150 g was made to overflow into the successive reactor vessel. A mixture consisting of 240 parts by weight of m-xylene and 60 parts by weight of t-BHPO as used in Example 1 was continuously supplied to the first reactor vessel at a rate of 300 g/hr, and air was blown into the respective reactor vessels each at a flow rate of 10 l/hr. The autooxidation reaction was continuously carried out while keeping a temperature of reaction solution at 130° C. and a pressure at 10 kg/cm$^2$ gage in the respective reactor vessels. As a result, the reaction product solution was obtained from the fourth reactor vessel at a rate of 303.5 g/hr. As a result of analysis, it was found that a conversion of m-xylene was 7.9%, and a selectivity to m-methylbenzyl hydroperoxide was 72.8%.

EXAMPLE 10

300 g of distillate obtained by removing the oxidation product from the reaction product solution resulting from reaction conducted as in Examples 3, 4 and 5 by concentration under a subatmospheric pressure (the distillate consisting of 70.3% by weight of m-xylene, 22.3% by weight of t-BHPO, 5.1% by weight of t-butanol, 1.4% by weight of water, 0.2% by weight of acetone, and 0.7% by weight of others) was again charged into a titanium reactor, and subjected to a batchwise reaction at a reaction temperature of 120° C. under a reaction pressure of 10 kg/cm$^2$ gage for 5 hours while supplying air into the reactor at a flow rate of 10 l/hr, whereby a selectivity to m-methylbenzyl hydroperoxide of 82% was obtained at a conversion of m-xylene of 10.8%, while the amount of t-BHPO consumed was 1.7 g.

COMPARATIVE EXAMPLE 1

Oxidation was carried out in the same manner as in Example 1, except that 100 g of D-t-BPO (purity: 98%) was used in place of the t-BHPO solution, whereby 302.2 g of reaction product solution was obtained. As a result of analysis, it was found that p-xylene consumed amounted to 19.7 g, PX-HPO formed 12.1 g, p-tolualdehyde formed 2.4 g, p-methylbenzyl alcohol formed 0.8 g, and p-toluic acid formed 1.51 g. That is, a conversion of p-xylene was 9.85%, a selectivity to PX-HPO 47.2%, a selectivity to p-tolualdehyde 10.8%, a selectivity to p-methylbenzyl alcohol 3.5%, and a selectivity to p-toluic acid 6.8%, while the remaining D-t-BPO amounted to 89.4 g, and 8.6 g of D-t-BPO was consumed.

The present comparative example showed that, even if a large amount of D-t-BPO was used, the effect was low.

COMPARATIVE EXAMPLES 2–7

Oxidation was carried out in the same batchwise manner as in Example 1, while changing conditions to various degrees, and the results are shown in Table 2.

Comparative Examples 2, 4–6 show cases of using the well known initiators in the ordinary application range, Comparative Example 3 shows a case of using a large amount of the well known initiator as in Comparative Example 1, that is, corresponding to that within the application range of t-HPO according to the present invention, and Comparative Example 7 shows a case of using a small amount of t-BHPO, that is, using it within the ordinary application range as the initiator, and it was found that the effect was low in all the cases.

t-BHPO in Comparative Example 7 was used in the same solution form as in Example 1, where the amount added was in the weight as the solution.

TABLE 2

| Comp. Ex. | 2 | 3 | 4 | 5 | 6 | 7 |
|---|---|---|---|---|---|---|
| Kind of starting material | toluene | m-xylene | m-xylene | mesitylene | mesitylene | mesitylene |
| Initiator | D-t-BPO | D-t-BPO | D-t-BPO | D-t-BPO | azobisbutyronitrile | t-BHPO |
| Starting material charged g | 297 | 240 | 294 | 285 | 285 | 298 |
| Initiator charged g | 3 | 60 | 6 | 15 | 15 | 2 |
| Reaction pressure kg/cm$^2$ gage | 10 | 10 | 20 | 10 | 10 | 10 |
| Reaction temperature °C. | 150 | 130 | 150 | 140 | 140 | 150 |
| Air flow rate l/hr | 10 | 10 | 50 | 20 | 20 | 20 |
| Reaction time hr | 3.0 | 3.0 | 2.0 | 4.0 | 4.0 | 4.0 |
| Reaction product solution g | 304.4 | 302.2 | 301.9 | 303.1 | 300.3 | 305.8 |
| Starting material consumed g | 17.0 | 19.5 | 31.3 | 30.9 | 35.3 | 23.9 |
| Initiator consumed g | 2.1 | 15.1 | 4.9 | 12.5 | 15.0 | 2.0 |
| l-HPO formed g | 4.9 | 9.2 | 14.8 | 19.7 | 15.1 | 11.5 |
| Conversion % | 5.7 | 8.1 | 10.6 | 10.8 | 12.4 | 12.0 |
| Selectivity to l-HPO % | 21.3 | 36.2 | 36.3 | 50.3 | 33.8 | 38.0 |
| Reaction material | titanium | titanium | titanium | aluminum | titanium | alumi- |

We claim:
1. A process for producing an aromatic primary hydroperoxide selected from the group consisting of benzyl hydroperoxide, o-methylbenzyl hydroperoxide, m-methylbenzyl hydroperoxide, p-methylbenzyl hydroperoxide, 3,5-dimethylbenzyl hydroperoxide, and a mixture of 2,4-, 3,4- and 2,5-dimethylbenzyl hydroperoxide by oxidizing a methyl-substituted aromatic compound selected from the group consisting of toluene, o-xylene, m-xylene, mesitylene and pseudocumene in a liquid phase with a molecular oxygen-containing gas, which comprises carrying out the oxidation at 80° C.–150° C. and under a pressure ranging from atmospheric to 100 kg/cm² gage in the presence of 8–300 parts by weight of an aliphatic tertiary hydroperoxide having the formula:

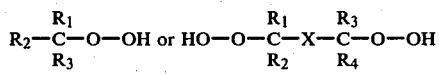

wherein $R_1$, $R_2$, $R_3$ and $R_4$ each represent alkyl groups having 1 to 4 carbon atoms, cycloalkyl groups or cycloalkyl groups having an alkyl group of 1 to 4 carbon atoms as a substituent and X represents alkylene groups having 1 to 4 carbon atoms per 100 parts by weight of the methyl-substituted aromatic compound.

2. A process according to claim 1, wherein the oxidation is carried out in the presence of 8–100 parts by weight of the aliphatic tertiary hydroperoxide per 100 parts by weight of the methyl-substituted aromatic compound.

3. A process according to claim 1, wherein the aliphatic tertiary hydroperoxide is at least one of t-butyl hydroperoxide, p-methane hydroperoxide, and 2,5-dimethylhexane-2,5-dihydroperoxide.

4. A process according to claim 1, wherein the aliphatic tertiary hydroperoxide is in solution.

5. A process according to claim 1, wherein the oxidation is carried out at 100°–140° C.

6. A process according to claim 1, wherein the oxidation is carried out under a pressure of 2–30 kg/cm² gage.

7. A process according to claim 1, wherein the molecular oxygen-containing gas is air.

8. A process according to claim 1, wherein the oxidation is carried out batchwise, semi-batchwise, or continuously.

9. A process according to claim 1, wherein the oxidation is carried out further in the presence of a small amount of an initiator.

10. A process according to claim 9, wherein the initiator is di-t-butyl peroxide, azobisisobutyronitrile or benzoyl peroxide.

11. A process according to claim 9, wherein 0.1–5 parts by weight of the initiator is present per 100 parts by weight of the methyl-substituted aromatic compound in a batchwise reaction.